United States Patent [19]
Faranda

[11] Patent Number: 5,467,147
[45] Date of Patent: Nov. 14, 1995

[54] OPHTHALMIC TREATMENT AID HAVING A PRESSURE APPLICATOR

[76] Inventor: Carmen Faranda, 7295 Trenton Pl., Ravenna, Ohio 44266

[21] Appl. No.: 280,367

[22] Filed: Jul. 26, 1994

[51] Int. Cl.[6] .................................................. G02C 1/00
[52] U.S. Cl. ........................... 351/41; 351/158; 351/246
[58] Field of Search ........................... 351/158, 41, 247, 351/246; 424/427, 429

[56] References Cited

U.S. PATENT DOCUMENTS

| | | |
|---|---|---|
| 780,563 | 1/1905 | Girard . |
| 2,757,665 | 8/1956 | Tanikawa . |
| 2,965,099 | 12/1960 | Aufricht . |
| 3,976,072 | 8/1976 | Walker . |
| 4,457,757 | 7/1984 | Molteno . |
| 4,886,488 | 12/1989 | White . |
| 4,959,048 | 9/1990 | Seder et al. . |
| 5,030,214 | 7/1991 | Spector . |

*Primary Examiner*—William L. Sikes
*Assistant Examiner*—Hung Xuan Dang
*Attorney, Agent, or Firm*—Watts, Hoffmann, Fisher & Heinke Co.

[57] ABSTRACT

An apparatus and method for facilitating treatment of the eye with topical medication by temporarily controlling fluid flow from the eye by way of compression of the proximal lacrimal drainage system. A support structure, such as an eyeglass frame, is adapted to be worn in a substantially stationary position on a user's face. Attached to the support structure is a pressure applicator for exerting gentle, external pressure near the patient's eye in a region at which lacrimal flow from the eye is temporarily inhibited by the pressure applicator. The pressure applied is of the order of magnitude which can comfortably be digitally exerted, and is focused on the exterior of the lower eyelid near the nose, in order to temporarily obstruct fluid flow through the nasolacrimal duct. The pressure applicator is a pliable, resilient pod having an ovoid shape, on the order of 1.0 inch in length and 0.75 inches in width. Where only one eye is treated, only one pressure applicator is necessary. Where both eyes are to be treated simultaneously, a matching pair of pressure applicators is employed. The pressure applicators are attached to the frame front portion of the eyeglass frame, at a location at which the frame would normally accommodate nose pads. In use, the apparatus is donned immediately after administration of topical eye medication, and is worn for several minutes, i.e., five to ten minutes being typical, for temporarily blocking or inhibiting lacrimal flow until the topical eye medication has mainly been absorbed into the eye itself, at which time the apparatus can be removed until the next administration of the topical medication.

15 Claims, 2 Drawing Sheets

OPHTHALMIC TREATMENT AID HAVING A PRESSURE APPLICATOR

BACKGROUND OF THE INVENTION

1. Technical Field

This invention relates generally to the field of ophthalmology, and more particularly to an aid for inhibiting passage of topically applied eye medication into the patient's bloodstream.

2. Background Art

Topical medications, in the form of drops or ointment, are frequently used in treatment of many eye disorders, such as glaucoma. Though such medications are beneficial when restricted to the immediate region of the eye itself, some of them, if absorbed into the patient's bloodstream, can cause profound negative side effects in many different parts of the body, such as the heart, pulmonary system, liver, pancreas, brain, and can even result in sexual disfunction.

Topical eye medications can make their way into the patient's bloodstream by way of the lacrimal system of each eye. The lacrimal system includes glands and structure for both producing beneficial tears, and for drainage of tears from the eye.

The space between the exterior of a normal eye and the interior of surrounding tissues can accommodate only about ten microliters of fluid, be it tears or artificially introduced fluid such as topical eye medication. A normal drop from a medicine dropper or bottle ranges from about 25 to 50 microliters. It can therefore be seen that, when topical eye medication is administered, the volume of the medication far exceeds the capacity of the eye to accommodate the extra fluid. It is therefore evident that a relatively large fraction of the administered medication will drain from the eye through the lacrimal system and into the patient's nasal cavity.

Tears, a complex solution, are produced by lacrimal glands located under the eyelids. Excess tears are both dissipated by evaporation and by drainage through the lacrimal system. The lacrimal system includes upper and lower puncta, located on the interior of the upper and lower eyelids, respectively. The puncta are orafi which communicate respectively with canalicular canals, which in turn lead to a lacrimal tear sac. The tear sac communicates with a channel known as the nasolacrimal duct, which leads into the patient's nasal cavity. The nasal cavity is lined with thin mucus membrane which has a high facility for absorbing incident chemicals into the patient's bloodstream.

Therefore, when topical eye medication is administered, some of it is carried away by the natural flow of tears and ends up in the patient's nasal cavity, from which a certain amount of that medication is subsequently absorbed into the patient's bloodstream through the nasal mucosa. Carried by the bloodstream, the medication makes its way to virtually all parts of the patient's body. If the medication is of a type which can cause negative side effects, such transport is undesirable.

Movement of fluid through the lacrimal system is assisted by blinking of the eyes. This phenomenon is sometimes referred to as "the lacrimal pump". Conversely, if the eyes are kept gently closed, fluid movement through the lacrimal system is usually reduced.

It is known that, when topical eye medication is administered, much of the dose is actually absorbed into the eye within a few minutes after administration. Therefore, it is possible to reduce the amount of medication which is transmitted by the lacrimal system into the patient's nasal cavity and subsequently into his bloodstream by inhibiting only temporarily the flow of tears through the lacrimal system into the patient's nasal cavity. Usually, inhibiting lacrimal flow for about five minutes after administering topical eye medication is sufficient to satisfactorily reduce the amount of medication which ultimately ends up in the patient's bloodstream.

It is known that a patient can inhibit his lacrimal flow by the use of gentle digital pressure, usually applied in the general area of the eyelids nearest the nose. For patients with arthritis, long fingernails or disorders making hands unsteady, this technique has disadvantages, and sometimes cannot be practiced at all.

Physicians sometimes recommend that a patient keep his eyes gently closed after administering topical eye medication. This advice is intended to reduce the amount of lacrimal flow, and therefore to correspondingly reduce the amount of eye medication delivered to the patient's nasal cavity by the pumping action which blinking would otherwise cause.

Surgically implanted devices are known for either partially or totally obstructing lacrimal flow. These devices, however, are designed as permanently in-dwelling implements, and are not designed to be readily removed except by an appropriately trained physician. They do not, therefore, lend themselves to temporary, short-term reduction of lacrimal flow. Rather, such implements are designed for patients who have a condition often called "dry eye", in order to reduce drainage of lacrimal fluid from the eye and, therefore, facilitate retention of tears keeping the eye moist.

A general object of the present invention is to provide apparatus and method for facilitating topical eye treatment by controlling fluid flow through the lacrimal system without the need for application of digital pressure.

DESCRIPTION OF THE INVENTION

The disadvantages of the prior art are reduced or eliminated by a medical eye treatment aid including a support structure configured to be worn on a patient's face in a substantially stationary position near at least one of the patient's eyes, and a pressure applicator mounted on the support structure and positioned for applying gentle external pressure near the patient's eye for inhibiting fluid flow through the lacrimal system of the eye when the support structure is worn on the patient's face in the above-mentioned substantially stationary position.

The treatment aid of this invention is donned immediately after administration of topical medication to an eye. During the wearing period, the pressure applicator inhibits fluid flow exiting the eye through the lacrimal system. This reduces or prevents absorption of the eye medication into the patient's bloodstream via the nasal cavity. When a few minutes have elapsed since administration of the eye medication, and the medication has had time to be absorbed mainly by the eye itself which it is intended to treat, the treatment aid can be removed until the next administration of topical medicine.

In accordance with a more specific feature of the invention, the support structure comprises a pair of eyeglass frames having two temple portions hinged to a frame front portion. The pressure applicator is mounted on the frame front in a position at which the frame front would normally carry a nose pad.

When a user dons the eyeglass frames, the pressure applicator gently impinges against the exterior of the lower eyelid near the nose. This gentle pressure tends to temporarily compress and close off the nasolacrimal canal, which inhibits fluid flow through the lacrimal system and into the patient's nasal cavity.

In addition, the pressure applicator also impinges to some extent gently against the upper eyelid which serves to hold the eyelids closed in a relaxed position. This feature reduces the stimulation of fluid flow through the lacrimal system that is caused by blinking, squinting or fluttering the eyelids.

Therefore, the present invention inhibits fluid flow through the lacrimal system by both impinging on a portion of the lacrimal system and by maintaining the eyelids in a relaxed closed position.

According to a more specific feature of the invention, the pressure applicator is a pliable, resilient pod which is generally ovoid in shape. The pod is about 1.00 inch in length and about 0.75 inches in width. It is about the size of a grape.

Thus far, a treatment aid having only one pressure applicator has been described. Where both eyes are to be treated, a second pressure applicator is used. The second pressure applicator is positioned on the frame front at a location which is approximately symmetrical with respect to the location of the first pressure applicator, i.e., at a location at which the frame front would normally have another nose pad.

The invention will be understood in more detail by reference to the following detailed description, and to the drawings, in which:

BEST MODE FOR CARRYING OUT THE INVENTION

Figure 1:
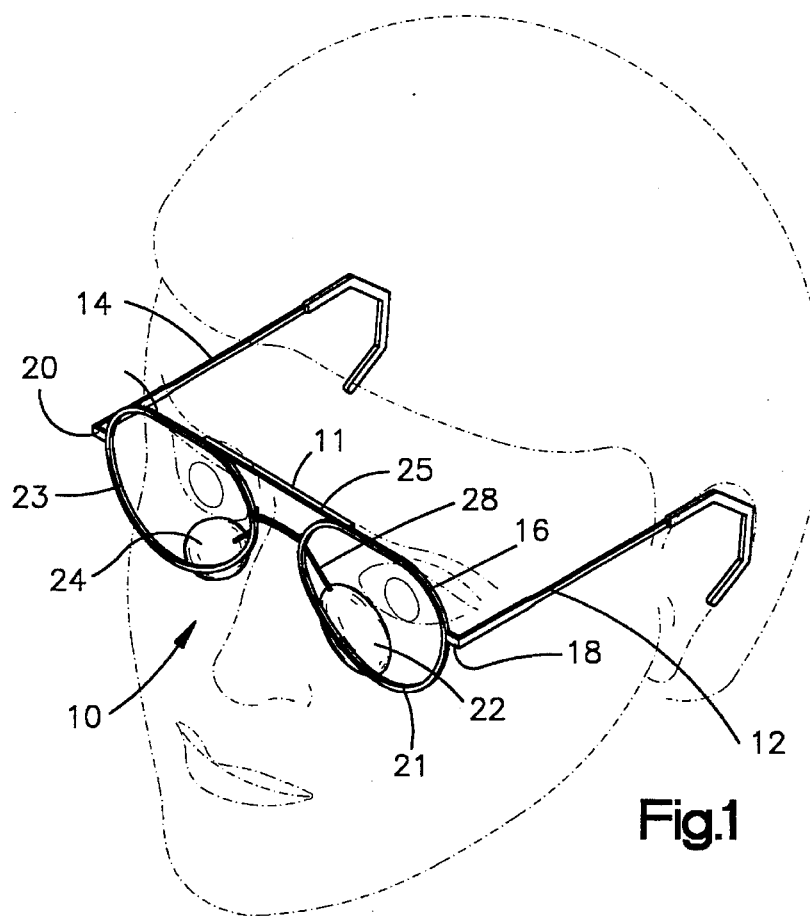
FIG. 1 is a perspective view of one embodiment of the present invention.
Figure 2:
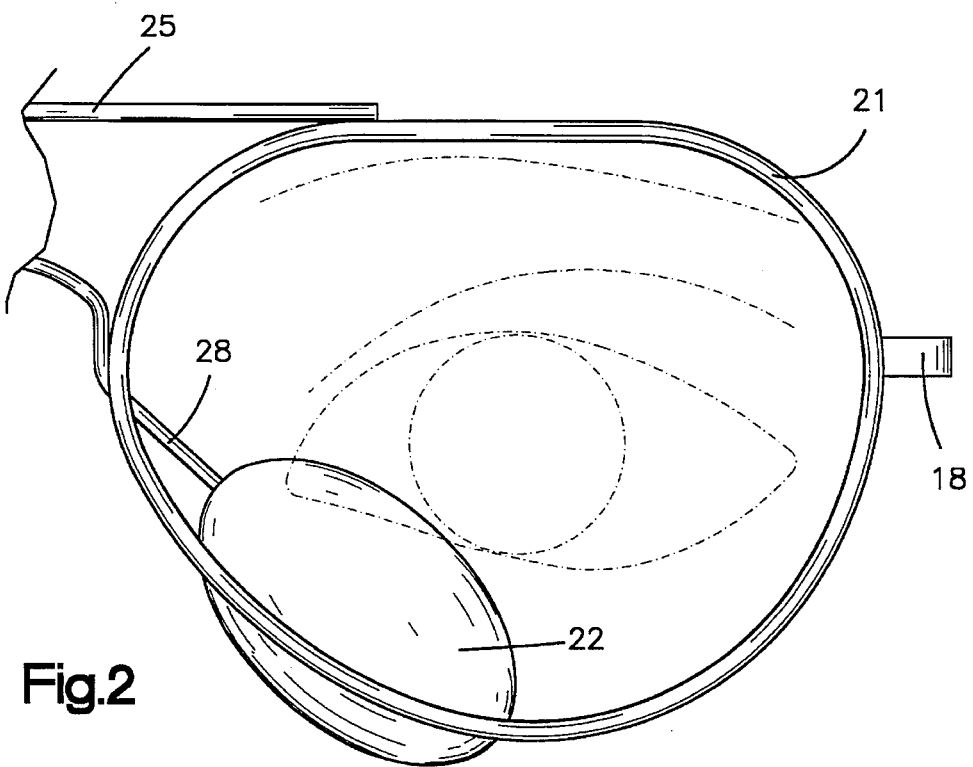
FIG. 2 is a detailed view showing a portion of the embodiment of FIG. 1.

Referring to FIGS. 1 and 2, an ophthalmic treatment aid in accordance with the invention is shown.

A support structure, comprising an eyeglass frame 10, is shown. The eyeglass frame 10 includes a pair of temple portions 12, 14. The eyeglass frame also includes a frame front portion. The temple portions 12, 14 are connected respectively to opposite sides of the frame front portion 16 by way of hinge structure 18, 20, respectively.

The frame front portion includes a pair of peripheral rims 21, 23 which normally accommodate eyeglass lenses. The peripheral rims 21, 23 are joined by a bridge portion 25.

The eyeglass frame is sized such that it can be worn in a conventional manner by a human patient. When worn, the temple portions are hooked over the user's ears, with the frame front portion being disposed generally in front of the eyes of the user.

Since, as will be explained in more detail below, the user's eyes are normally closed when utilizing the ophthalmic treatment aid, there is no need that the frame front portion actually contain eyeglass lenses.

A pair of pressure applicators 22, 24 are also shown. The pressure applicators are attached to the frame front at locations at which the frame front would normally accommodate nose pads. Each pressure applicator is attached to a projection extending inwardly from the frame front, and which is of a type suitable for use in supporting nose pads. A projection is indicated by reference character 28.

The pressure applicators can be adhered to the projections by means of suitable adhesive. They can also be mounted on the frame front portion by suitable mechanical arrangement, the design of which is well within the ordinary skill in the art. The pressure applicators can be also, if desired, adhered directly to the frame front portion by the use of suitable adhesive, without the need for the projection 28.

Alternately, the pressure applicators can actually be fitted over nose pads on a conventional pair of eyeglass frames.

The pressure applicators 22, 24 are made of a pliable resilient material. Foam can be used, or a resilient soft plastic shell. The invention, however, is not to be limited to these materials, the materials being enumerated only by way of example. Other appropriate materials are capable of selection by those of ordinary skill.

The pressure applicators 22, 24 are generally ovoid in configuration. They are about 1.0 inches in length, and about 0.75 inches in width.

The pressure applicators are positioned on the inside of the frame front portion, toward the nose, and slightly below center. In such a position, when the user dons the eyeglass frames, the pressure applicators gently press externally against the region of the lower eyelid near the nose, and, to some extent, also externally against the upper eyelid in the area nearest the nose. Thus, the pressure applicator presses gently against the inner corner of the eye.

The positioning of the pressure applicators, and their relative hardness or softness, is selected to mimic a magnitude of pressure against the external portions of the eyelids near the nose which would be applied by a user using moderate digital pressure.

The pressure applicators, when worn, perform at least two beneficial functions. First, they press against the portion of the lacrimal system which is generally known as the nasolacrimal duct. This pressure causes the duct to compress such that fluid flow through the duct is inhibited, or completely cut off, temporarily, while the treatment aid is worn. Additionally, by pressing gently against the exterior of the upper eyelid, the pressure applicator gently holds the eye closed and stationary, avoiding blinking, squeezing, squinting, fluttering or the like. The feature of holding the eye closed avoids stimulation of fluid flow through the lacrimal system which normally would be caused by motion of the eyelids and nearby tissues.

In using the ophthalmic treatment aid, the user, or patient, first administers topical eye medication, for example, in the form of drops or ointment, into the desired eye. Medication can be administered to one or both eyes, as the patient's condition requires.

In situations in which the patient needs to treat only one eye, only one pressure applicator is necessary. Where both eyes require treatment, the pair of pressure applicators, as described above, is used.

Immediately following administration of the eye medication, the patient puts on the treatment aid. The treatment aid, by compressing a portion of the lacrimal system, such as the nasolacrimal duct, and by holding the eyelids in a gently closed attitude, reduces or substantially entirely stops flow of fluid, including eye medication, through the lacrimal system and into the patient's nasal cavity. This inhibition or cessation of flow substantially reduces exposure of the nasal mucus membranes to the eye medication and, therefore, substantially limits the amount of eye medication which reaches the patient's general bloodstream. This is beneficial because, in the instance of eye medications which may have serious negative side effects, those side effects can be reduced or eliminated by preventing passage of the medication into the patient's bloodstream.

The treatment aid is worn only temporarily, i.e., for a few minutes after administration of the topical medication. During these few minutes, the eye medication is absorbed into the eye itself, its intended destination, so that the main portion of its effect is beneficially focused on the eye itself. After 5–10 minutes have elapsed following administration of the eye medication, the treatment aid can be removed until the next administration of eye medication.

It should be emphasized that, for best results, the temple portions of the eyeglass frames should be configured to curve around a substantial portion of the user's ears so that the temples can exert a gentle force tending to maintain the frame front portion in a stationary position on the patient's face, and also to provide the gentle pressure needed for the impingement of the pressure applicators against the patient's nasolacrimal duct or other portion of the lacrimal system.

Figure 3:
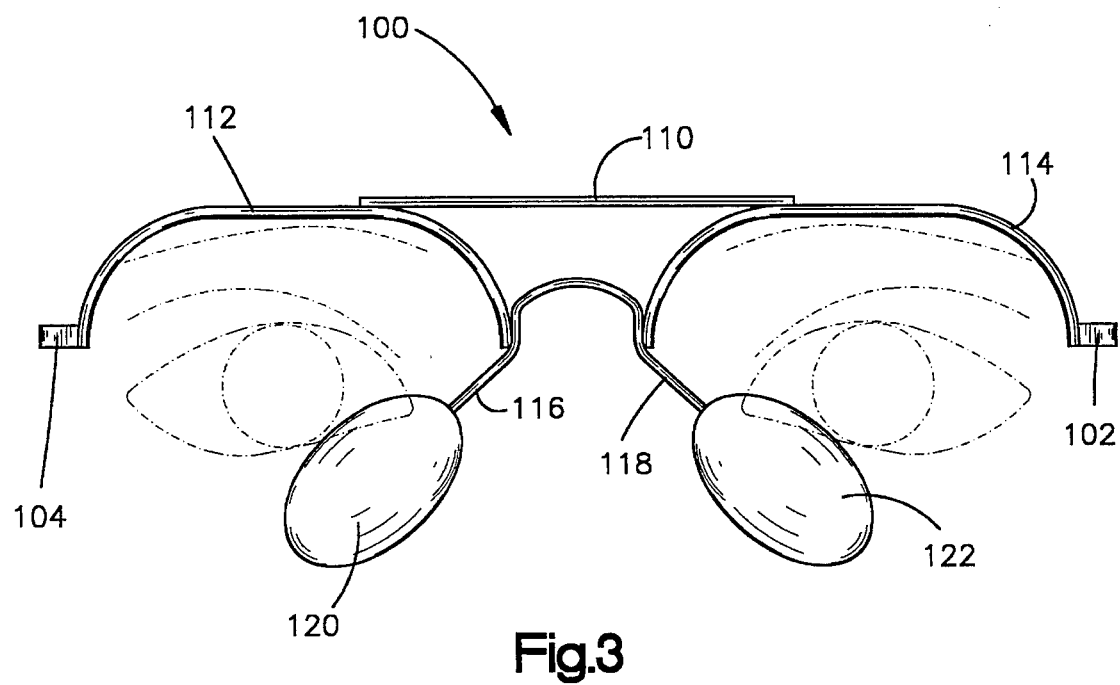
FIG. 3 is a front plan view illustrating a second embodiment of the invention.

FIG. 3 illustrates another embodiment of the present invention.

FIG. 3 shows an adapted version of a support structure 100. This adapted version of the support structure includes a pair of temples (not shown) which are hinged to the support structure 100 at hinge points 102, 104, similar to those described and shown in connection with the previously discussed embodiment. The temples are hinged to the support structure 100 which is adapted to fit across the patient's face in a substantially stationary position when the temples are hooked behind the patient's ears.

The support structure 100 includes a bridge portion 110, and generally horizontal extending portions 112, 114, each of which extends between the bridge portion and a respective one of the hinge portions 102, 104.

The support structure 100 also includes a pair of projections 116, 118 which extend toward the user's face when he dons the support structure apparatus. These projections are similar to those described in connection with the previously discussed embodiment. Likewise, a pair of pressure applicators 120, 122 are mounted in a suitable fashion on the projections 116, 118. The pressure applicators are substantially the same as those described in connection with the previously discussed embodiment. Likewise, the location of the pressure applicators, when mounted on the support structure 100, is designed to be equivalent to the locations of the pressure applicators described in the preceding embodiment.

While a specific embodiment of the present invention has been described with some particularity, it is to be understood that those of ordinary skill in the art may be able to make certain additions or modifications to, or deletions from, the specifics of the described embodiment, without departing from the spirit or the scope of the claims, as set forth below.

I claim:

1. An ophthalmic treatment aid comprising:
   a) support structure configured to be worn on the face of a patient in a stationary position near an eye; and
   b) a pressure applicator mounted on said support structure for applying gentle external compressive pressure for inhibiting fluid flow through the lacrimal system of said eye when said support structure and said pressure applicator are worn in said stationary position.

2. The treatment aid of claim 1, further comprising:
   additional pressure applicator for simultaneously temporarily applying gentle external pressure for inhibiting fluid flow through the lacrimal system of the patient's other eye.

3. The treatment aid of claim 1, wherein:
   said support structure comprises an eyeglass frame including temple portions hinged to a frame front portion, wherein said pressure applicator is mounted on said frame front portion.

4. The treatment aid of claim 3, wherein:
   said pressure applicator is attached to a portion of said frame front which would normally accommodate a nose pad.

5. The treatment aid of claim 1, wherein:
   said pressure applicator comprises a pliable pod having a generally ovoid shape.

6. The treatment aid of claim 5, wherein:
   said pressure applicator is about 1.0 inch in length and about 0.75 inches in width.

7. The treatment aid of claim 1, wherein:
   said pressure applicator is located for compressing the nasolacrimal duct.

8. The treatment aid of claim 1, wherein:
   said pressure applicator applies external pressure to maintain the eyelids closed.

9. The treatment aid of claim 1, wherein:
   said pressure is comparable to the amount of pressure which can comfortably be digitally applied.

10. The treatment aid of claim 1 wherein said pressure applicator is adapted to apply external pressure for compressing a nasolacrimal duct near said eye.

11. Apparatus for facilitating eye treatment, said apparatus comprising:
    a) an eyeglass frame including two temple portions hinged to a frame front portion; and
    b) a resilient pressure applicator mounted on said frame front portion in a region normally accommodating nose pads, said pressure applicator being positioned for temporarily applying external pressure for inhibiting fluid flow through the lacrimal system of a human patient's eye when said eyeglass frame apparatus is worn by the patient.

12. The apparatus of claim 11, further comprising:
    a second pressure applicator mounted on said frame front portion for temporarily applying pressure for inhibiting fluid flow through the lacrimal system of the other eye of the patient.

13. The apparatus of claim 11, wherein:
    said pressure applicator comprises a pliable plastic member having a generally ovoid configuration.

14. A method for facilitating ophthalmic treatment by the use of topical eye medication, said method comprising the steps of:
    a) applying the topical medication to the eye; and
    b) temporarily applying gentle external pressure to the region near the eye in a location for inhibiting lacrimal flow from the eye by use of a mechanical pressure applicator.

15. The method of claim 14 wherein said mechanical pressure applicator is used to temporarily apply external pressure for compressing a nasolacrimal duct near the eye.

* * * * *